United States Patent [19]
McAdams et al.

[11] Patent Number: 5,337,748
[45] Date of Patent: Aug. 16, 1994

[54] BIOSIGNAL ELECTRODE

[76] Inventors: Eric T. McAdams, Ormsdale, 52 Cabe Road, Whitehead, County Antrim BT38 9PZ; James A. McLaughlin, 9 Hampton Gardens, Hamilton Court Village, Belfast TB7 30F; John McC. Anderson, 19 Torngrange, Hollywood, County Down BT18 0NG, all of Northern Ireland

[21] Appl. No.: 838,219
[22] PCT Filed: Oct. 11, 1990
[86] PCT No.: PCT/GB90/01565
§ 371 Date: Mar. 10, 1992
§ 102(e) Date: Mar. 10, 1992
[87] PCT Pub. No.: WO91/05509
PCT Pub. Date: May 2, 1991

[30] Foreign Application Priority Data
Oct. 11, 1989 [GB] United Kingdom ............. 8922836.5

[51] Int. Cl.⁵ .................................................. A61B 5/04
[52] U.S. Cl. ....................... 128/640; 128/641; 607/149; 607/152
[58] Field of Search ............... 128/640, 641, 798, 802, 128/803; 607/149, 152, 153

[56] References Cited

U.S. PATENT DOCUMENTS

| | | |
|---|---|---|
| 3,982,529 | 9/1976 | Sato . |
| 4,269,189 | 5/1981 | Abraham ............... 128/798 |
| 4,300,575 | 11/1981 | Wilson . |
| 4,370,984 | 2/1983 | Cartmell . |
| 4,393,584 | 7/1983 | Bare et al. . |
| 4,640,289 | 2/1987 | Craighead . |
| 4,736,752 | 4/1988 | Munck et al. ........ 128/798 |
| 4,763,660 | 8/1988 | Kroll et al. .......... 128/640 |
| 4,838,273 | 6/1989 | Cartmell ............. 128/640 |
| 4,934,383 | 6/1990 | Glumac .............. 128/802 |

FOREIGN PATENT DOCUMENTS 2345981 3/1977 France .
1575364 9/1980 United Kingdom .

*Primary Examiner*—Lee S. Cohen
*Attorney, Agent, or Firm*—Sughrue, Mion, Zinn, Macpeak & Seas

[57] ABSTRACT

A biosignal electrode 10 which comprises a flexible substrate 1 having an obverse side and a reverse side, the obverse side having printed thereon an electrically conductive layer 2 comprising an ink having electrically conductive particles or mixture of particles therein, the layer in plan comprising a first or sensor end 11, a second or connecting end 12 and an interconnecting portion 13, and the sensor end in plan resembling a hollow figure.

21 Claims, 4 Drawing Sheets

BIOSIGNAL ELECTRODE

BACKGROUND OF THE INVENTION

This invention relates to a surface electrode which can be used medically to receive and transmit biosignals emanating from a body or to apply low level electrical signals to the body.

Medical surface monitoring electrodes are well known. For example, one such electrode consists of a silver-plated eyelet which is housed within a recessed plastic element or cup. A snap fastener stud is located on the outside to the plastic element and acts as a means of connecting the external circuitry to the electrode. In this type of electrode there is a sponge which has been impregnated with an electrolytic gel and which is located within the plastic electrode housing so that when in use the sponge serves as a conductive bridge between the eyelet and the patient's skin. The electrolytic gel enhances the conductivity of the skin and ensures good electrical contact between the patient and the metal sensor. Since the electrode system must have good contact with the skin, the present technology provides that the plastic housing incorporating the eyelet sensor, with its conductive gel, be attached to a disc of open cell plastic foam or microporous tape, which is coated on its underside with a medical-grade contact adhesive. This resilient adhesive disc serves to attach the system to, and hold it on the patient's skin. Finally, for storage purposes a cap is placed over the rigid plastic element in order to isolate the electrode from the atmosphere and thus prevent the drying-out of the conductive gel, which is water based.

Electrodes of the type just described have proven quite reliable in establishing an electrical connection to the patient but associated with them are several disadvantages. Firstly the design incorporates many components which render the electrode somewhat complex in assembly and therefore relatively expensive to manufacture. Secondly it has a large profile, covers a considerable skin area and lacks flexibility. This rigidity of the element, or housing, can give rise to skin abrasion and irritation and pull on the connecting lead affects the sensor and can give rise to motion artefact signals.

Recently a simpler, less expensive, electrode design has become available and it employs a metal foil which acts as both an electrode sensor and as a means of connection to the external circuitry. The connection to the metal foil is via an exposed tab of foil which in general practice is grabbed by a small alligator clip.

In this newer type a solid, adhesive, hydrogel serves both as the electrolyte and the adhesive means to the skin. The system has electrode flexibility, the desired low profile and it conforms well to body contours. Since the system dispenses with the conventional disc of adhesive backing, the overall electrode area is small. This electrode design is simple and less expensive to manufacture.

Although it is an improvement on the metal eyelet electrode system this metal foil electrode has a major disadvantage in that the foils generally used are not silver, because of expense, and therefore have relatively poor electrical properties. The cost of this electrode is still not sufficiently low.

SUMMARY OF THE INVENTION

What is required therefore is a relatively inexpensive electrode for biosignal monitoring which has a high electrical performance and which is small, thin, flexible and relatively easy to produce.

The invention, therefore, provides a biosignal electrode which comprises a flexible substrate having an obverse side and a reverse side, the reverse side having printed thereon an electrically conductive layer comprising an ink having electrically conductive particles or mixture of particles therein, the layer in plan comprising a first or sensor end, a second or connecting end and an interconnecting portion, the sensor end in plan resembles a hollow figure, the substrate at or near the sensor end being continuous and imperforate.

Preferably, the figure is a curved shaped figure.

Preferably, the figure is a closed figure.

Preferably, the particles comprise silver or tin.

Preferably, the mixture of particles comprises silver/silver salt or tin/tin salt.

BRIEF DESCRIPTION OF THE DRAWINGS

The invention will be understood in greater detail from the following description of a preferred embodiment thereof given by way of example only and with reference to the accompanying drawings in which.

DETAILED DESCRIPTION OF THE PREFERRED EMBODIMENTS

Figure 1:
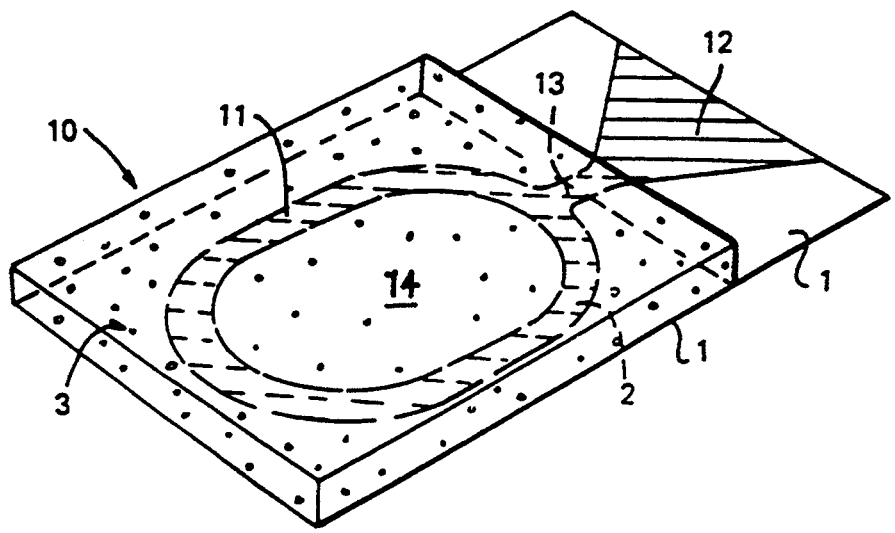
FIG. 1 is a perspective view of a first embodiment of an electrode according to the invention.
Figure 1A:
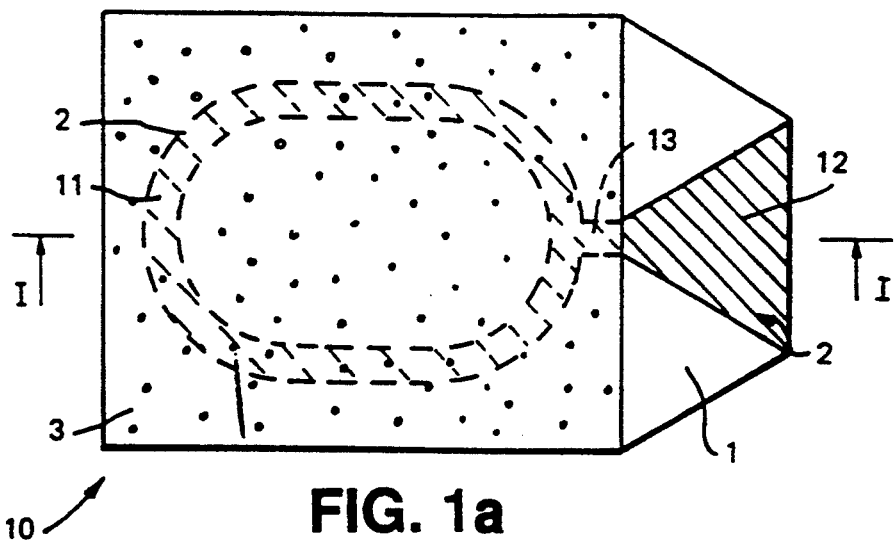
FIG. 1a is a plan view of a first embodiment of an electrode according to the invention.
Figure 1B:
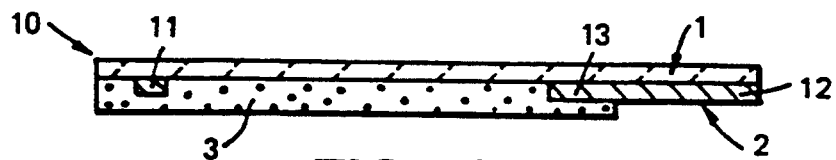
FIG. 1b is an elevation of the electrode of FIG. 1 of the drawings taken along the line I—I and viewed in the direction of the associated arrows.

Referring to the drawings and in particular to FIGS. 1, 1a and 1b there is shown a biosignal electrode 10 which comprises a flexible substrate 1 having an obverse side and a reverse side. On the obverse side is printed a shaped or patterned electrically conductive layer 2. The conductive layer 2 comprises a first or sensor end 11, a second or connection end 12 and an intermediate portion 13. The sensor end 11 in plan represents a hollow figure. In the present embodiment, the sensor end 11 is oval in plan or is a figure represented in plan by two semicircles the opposing free ends of which are connected by respective lines in substantially parallel spaced apart relationship having a centrally located void 14 completely enclosed by the sensor end 11. Leading from the sensor end 11 and contiguous there-with is the intermediate portion 13 which terminates in the connection end 12 also contiguous with the intermediate portion 13. The connection end or electrode stem 12 is delta shaped in plan view.

The conductive layer 2 is applied by printing, preferably screen printing, an ink having electrically conductive particles or a mixture of particles. The particles may comprise silver or tin. The mixture of particles may comprise silver/silver salt or tin/tin salt. Preferably, the salt is chloride with the most preferred being silver/silver chloride.

The conductive layer 2 is relatively thin being of the order of from 5–15 microns.

On top of the sensor end 11 is coated a conductive adhesive layer 3 which performs the dual function of enabling good electrical contact to take place between the patient's skin and the sensor end 11 and maintaining the sensor end 11 in firm contact with the patient's skin. Accordingly the layer 3 is not restricted to covering just the sensor end 11 per se or to having the same form or area. Rather the layer 3 covers the sensor end 11 and that part of the substrate 1 in the vicinity of the sensor end 11. The shape and area of layer 3 will be determined by manufacturing, cost and performance constraints. The connection end 12 does not have the layer 3 thereon. The composition of the layer 3 can be based on either natural or synthetic hydrocolloids such as Karaya, modified acrylic resins or similar materials.

Monitor connection can be made to the electrode connector end 12 via an alligator clip or similar device. Alternatively, a lead may be bonded to the electrode stem 12.

The figure or shape of the electrode sensor 11, the intermediate portion 13 and the connector 12 results in the deposition of a small fraction of the amount of conductive ink which would otherwise have been necessary to cover all the surface of substrate I thus resulting in considerable cost saving. The hollow sensor end 11 has the advantage of having a relatively large effective area whilst minimising the use of ink.

Given the small area and thinness of the layer 2, the electrode 10 in use is effectively radio transparent and it should not prove necessary to remove the electrode 10 prior to X-ray imaging of the patient.

The conductive adhesive layer 3 enables the electrode 10, whenever necessary, to be removed and reapplied or relocated without the need for regelling or without leaving a messy residue on the patient's skin.

When current passes through a gelled biomedical surface electrode, the major portion of the current flows through the peripheral area of the electrode. For example, in high current situations, such as in external cardiac pacing and defibrillation via large surface electrodes, serious skin burns and pain can occur under the edges of the electrode due to the localised high current density "hot spots".

Although it is not widely appreciated as evidenced by current monitoring electrode designs, a similar "edge" effect occurs in biosignal monitoring electrodes, albeit the current densities involved are much smaller and do not give rise to skin burns. This can be demonstrated by passing a small positive current through a silver sensor located in a saline bath and observing the deposition of silver chloride which intially takes place at the periphery of the sensor.

It has been found possible, therefore, in the present invention to provide the electrode 10 having a void 14 therein, thereby reducing manufacturing costs yet without significantly affecting the electrical performance of the electrode 10.

Figure 1C:
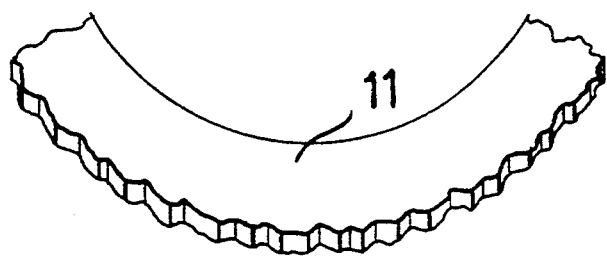
FIG. 1c is a partial perspective view of a roughened sensor edge according to an alternate construction.

The outer edge of the sensor 11 need not be smooth as shown on FIGS. 1, 1a and 1b. The outer edge of the sensor 11 may be made rough in order to increase the perimeter-to-area ratio and maximise the "edge" effect, as shown in FIG. 1c.

Current does not only flow through that part of the gel layer 3 directly below the sensor 11 but spreads out through the gel layer 3 generally beyond the perimeter of the sensor 11 and also within the enclosed void or hollow 14. The optimal sizes and shapes of the sensor 11 and the enclosed hollow 14 are therefore dependent on the dimensions of the gel layer 3 and should be chosen to enable the current flowing to spread through as large an area of the gel layer 3 as possible in order to minimise the electrode-gel-skin impedance.

Instead of one void 14 being enclosed within the sensor 11, several voids may be enclosed with similar electrical effect.

The shape of the void or hollow 14 need not have the same form as the periphery of the sensor end 11 and the inner and outer edges of sensor end 11 need not be in parallel spaced apart relationship as shown on FIGS. 1, 1a and 1b. For certain applications it may prove advantageous to have varying distances between the outer edge and the inner edge of the sensor end 11. The sensor end 11 may, for example, be wider at its remotest point from the connector end 12 as it is anticipated that this point or area will be subjected to the largest current densities.

The inner and outer edges of the sensor 11 may be shaped so as to form part of a commercial logo. Additional islands or elements (not shown) may be printed inside the void 14. These alterations and additions will not effect significantly electrode cost or performance.

It is well known that superior electrical performance is obtained at the electrode-electroylte interface when a silver, silver-plated or a silver coated sensor is coated electrolytically with a thin layer of silver chloride. Silver chloride is, however, a poor conductor and only a thin layer must be deposited if its advantageous characteristics or properties are not be outweighed by the increase in electrical resistance.

It has been found that where thin silver chloride layers are deposited electrolytically or otherwise onto a small area of silver, silver-plated or silver coated sensor, the silver chloride layers are readily removed upon the passage of current and electrical performance characteristics rapidly deteriorate. In the present invention, silver metal or tin metal particles may be incorporated into the ink composition used for printing the layer 2. However, given the relatively small area of the sensor end 11, it is preferred to use an ink having a mixture of silver/silver chloride particles which are dispersed throughout the ink and hence are dispersed throughout the layer 2. The performance of such inks resembles that of the well known sintered "pellet" silver-silver chloride sensors. The pellet sensor consists of a lead wire surrounded by a sintered silver-silver chloride cylinder which is formed by compressing and heat treating a mixture of silver and silver chloride powder. The Ag—AgCl "pellet" and ink sensors are less prone to the complete stripping of silver chloride upon passage of current than sensors with thin electrolytically deposited layers of silver chloride. It would also appear that silver-silver chloride sintered "pellets" and ink share similar silver/silver chloride ratios for optimal electrical performance, approximately 90% silver and 10% silver chloride by weight. The mixture of particles is dispersed throughout a suitable binder to make a high performance ink for biomedical electrode applications. The binder, for example, may be a thermoplastics material.

The composition of the layer 2 having silver/silver chloride therein provides superior electrical performances such as DC offset voltage, exchange current density, AC impedance, bias current tolerances.

The use of an ink having a mixture of tin/bin salts in particular stannous chloride may not provide as enhanced a performance when compared with a silver/silver chloride based ink. However, it will be appreciated that the tin/tin chloride based ink is considerably less expensive than the silver/silver chloride based ink and hence in those conditions where cost outweighs performance requirements, the tin/tin chloride based ink would be used.

Preferably, the silver/silver chloride based ink composition comprises micronised silver metal and silver chloride pigment. The tin/tin chloride base ink preferably comprises powdered tin metal and stannous chloride.

The surface topography of the layer 2 can affect the optimum electrical performance of the electrode 10. The rougher the surface, the lower the interface impedance. Optimal surface topography enables the use of a relatively small sensor area and a resultant saving in material costs. Surface roughness is optimised by suitable choice of aggregate particle size within the inks and screen mesh conformation. The cost can be further reduced by printing a first layer of ink (not shown) loaded with, for example, graphite or carbon and subsequently printing a relatively thinner layer 2 thereon. It is advantageous from a performance point of view if the first layer has a rough surface finish. Alternatively, the ink composition used in printing the layer 2 may also contain, for example, graphite, in order to lower cost.

The flexible substrate 1 may be a film forming material made from polyester, a polycarbonate or a nylon. Alternatively, the substrate 1 may comprise a a conductive, carbon black loaded film of polycarbonate sold under the Tradename "Makrofol.KL3-1009" by Bayer of West Germany.

Figure 2:
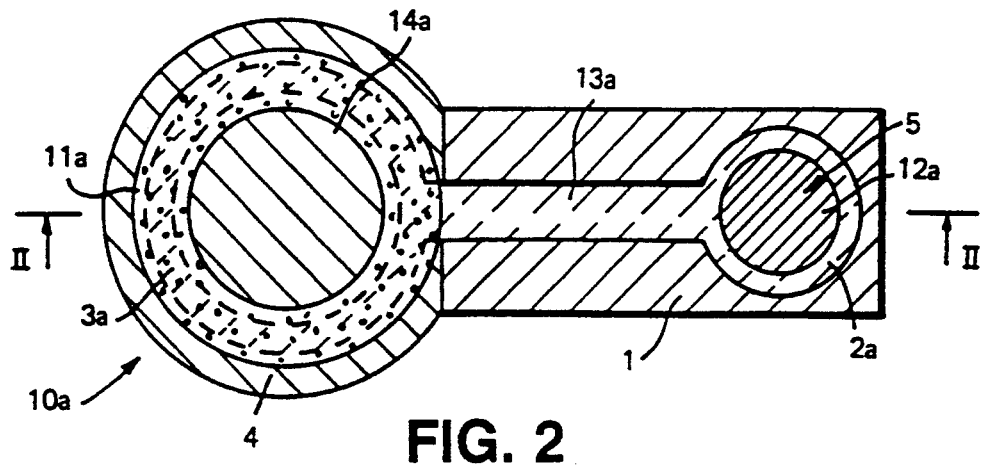
FIG. 2 is a plan view of a second embodiment of an electrode according to the invention.
Figure 2A:
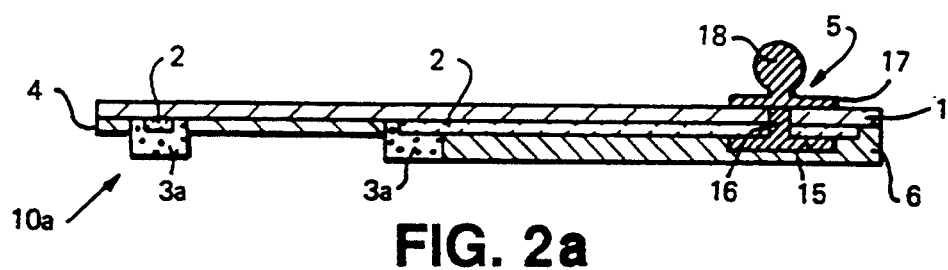
FIG. 2a is an elevation of the electrode of FIG. 2 of the drawings taken along the line II—II and viewed in the direction of the associated arrows.

An electrode 10a according to the invention is shown in FIGS. 2 and 2a of the drawings which is essentially similar to, and enjoys all the features of, the electrode 10 as described above. In the present embodiment, the sensor end 11a is in the form of an annulus 11a having a centrally located void 14a. The connection end 12a is disc-shaped in plan view.

On top of the sensor end 11a is printed preferably by screen printing an electrolytic gel layer 3a so that the sensor end 11a is interposed between the gel layer 3a and the substrate 1. Like the gel layer 3, the gel layer 3a serves to wet, and thus increases the conductivity of, the skin in the area to which it is applied and provides a conductive path between the patient and the conductive layer 2a and hence to the connection end or electrode stem 12a. The gel layer 3a may be an electrically conductive adhesive layer or a non-adhesive gel. The gel layer 3a should completely cover the sensor end 11a. It may be an annulus as shown in FIGS. 2 and 2a or an intact disc of any form which is convenient from a manufacturing point of view. The screen printing of such a layer 3a has obvious manufacturing advantages. Monitor connection can be made to the electrode stem 12a by means of an electrically conductive snap fastener 5. Alternatively, a lead wire (not shown) may be bonded to the stem 12a or the stem 12a may be used as a tab to which a monitor lead (not shown) is connected via an alligator clip or similar device (not shown).

The sensor end 11a can be held firm on the skin of the patient by the use of a layer 4 of medical grade contact adhesive coated onto the obverse side of the substrate 1 and in substantially co-planar relationship relative to the electrically conductive layer 2a. The adhesive layer 4 projects, in use, around the periphery of the sensor end 11a and through the void 14a of the sensor end 11a. In use, the adhesive layer 4 makes contact with the patient's skin around the sensor end 11a and through the void 14a.

Alternatively, the adhesive layer may be an overlapping layer of standard adhesive backing tape (not shown) and attached to the reverse side of the substrate 1.

A thin flexible insulating layer 6 is applied to the electrode stem 12a and to the intermediate portion 13a so as to ensure that only the sensor end 11a may be in electrical contact with the patient's skin. The insulating layer 6 is preferably in substantially co-planar relationship relative to the electrolytic gel layer 3 and may be of a conventional colophony type.

The connection end 12a has an opening through which is mounted the snap fastener 5. The snap fastener 5 is of sandwich construction having a first base 15 from which projects an upright portion 16. A second base 17 is provided which is in contact with the free end of the portion 16 and from which projects a snap-to-engage male end 18 of the fastener 5. The base 15 is in electrical contact with the layer 2a in the region of the connection end 12a with the upright portion 16 projecting through the opening therein. The second base 17 rests on the substrate 1 being, as indicated above, in electrical contact with the upright portion 16. The snap fastener 5 may be riveted in position. Accordingly, the sensor end 11a is in electrical contact with the male end 18. A cable (not shown) may be connected to the male end 18 for conveying signals to monitoring equipment (not shown).

With the connection end 12a offset from the sensor end 11a the motion artefact due to cable pull on the fastener 5 is minimised. The cable may also be connected and removed without disturbing the sensor-gel-skin system.

In neonatal and other applications it may be found useful to employ electrodes according to the invention where the connection is made via "flying leads" which can be bonded to the connection end 12a by, for example, conductive polymerizable adhesives. The use of a "flying lead" minimises the weight and profile of the electrode structure.

Alternatively, the lead may be bonded to the connection end 12a by means of a printed pad (not shown) of conductive bonding ink which is either uv curable or curable at low temperatures. An example of such a printable, conductive bonding ink is JL-43165 sold by Acheson Colloids Co. of Plymouth, United Kingdom. Using this means, a lead wire (not shown) may be bonded to the connection end 12a prior to curing and be in permanent electrical contact with the layer 2a following curing. Lead wires may be positioned robotically, thereby enabling a continuous on-line manufacturing process.

Figure 3:
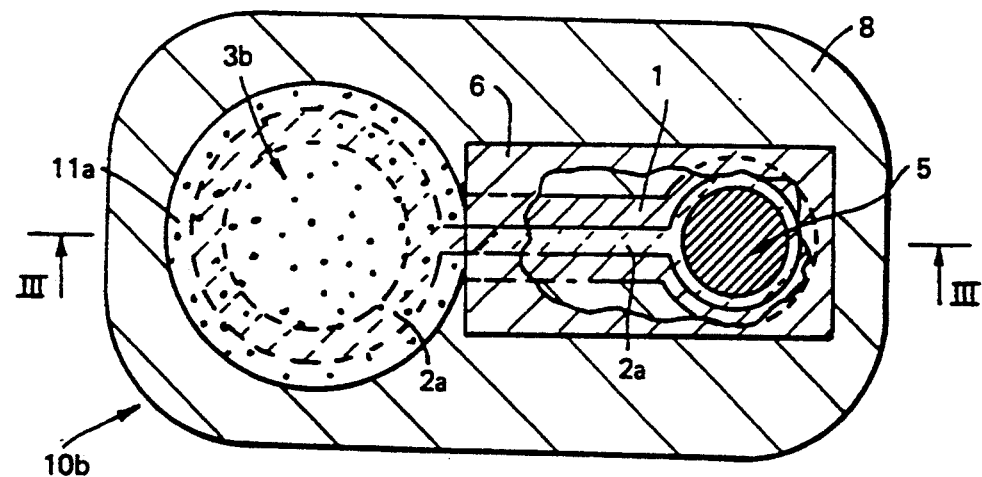
FIG. 3 is a plan view of a third embodiment of an electrode according to the invention.
Figure 3A:
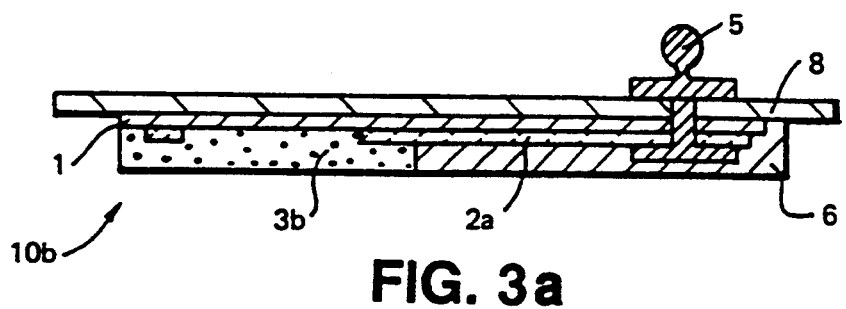
FIG. 3a is an elevation of the electrode of FIG. 3 of the drawings taken along the line III—III and viewed in the direction of the associated arrows.

An electrode 10b according to the invention is shown in FIGS. 3 and 3a of the drawings which is essentially similar to and enjoys all the features of the electrodes 10 and 10a as described above. However, the adhesive layer 4 is not in co-planar relationship relative to the electrically conductive layer 2; rather the equivalent layer comprises a backing tape 8 coated on the underside with a suitable medical grade adhesive which covers the reverse side of, and projects beyond, the substrate 1. The upright portion 16 of the fastener 5 projects through the adhesive layer 8. The second base 17 rests on the adhesive backing layer 8 being, as indicated in electrical contact with the upright portion 16.

A gel layer 3b is provided on the obverse side of the substrate 1, covering and making contact with the sensor end 11a. The gel layer 3b may be a circular disc as shown, or an annulus (not shown). The gel layer 3b may be a conductive adhesive, equivalent in composition to the gel layer 3 or to the gel layer 3a. Given the overlapping adhesive backing layer 8, it is not essential that the gel layer 3b be adhesive.

Alternatively, the substrate 1 may have a void therein in register with the void of the sensor end 11a so that, in use, the backing tape 8 passes through the substrate void and is in dermal contact with the patient.

Figure 4:
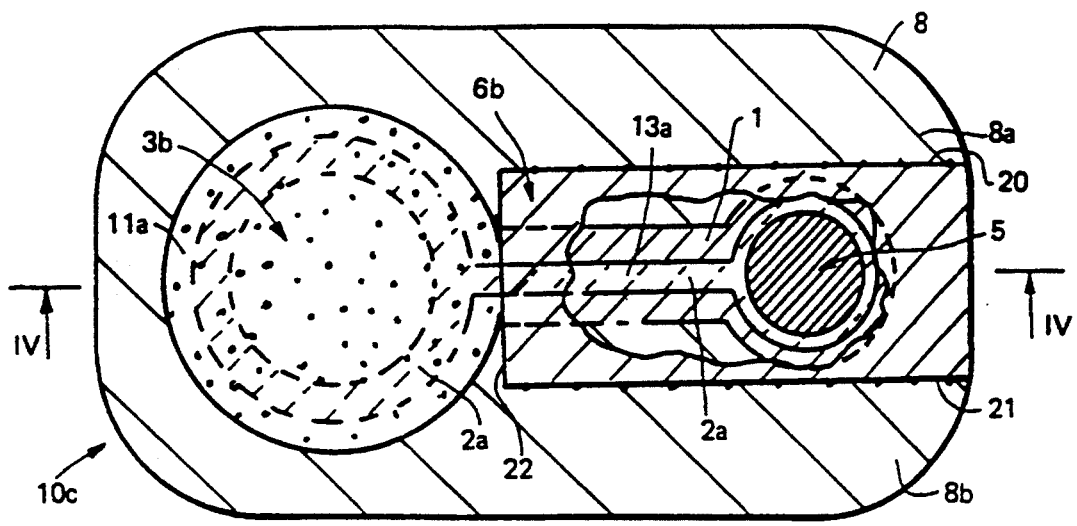
FIG. 4 is a plan view of a fourth embodiment of an electrode according to the invention.
Figure 4A:
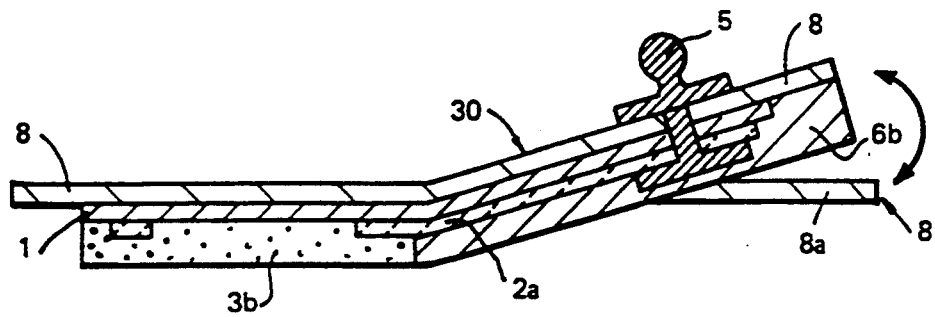
FIG. 4a is an elevation of the electrode of FIG. 4 of the drawings taken along the line IV—IV and viewed in the direction of the associated arrows.

In FIGS. 4 and 4a of the drawings, there is shown an electrode 10c according to the invention. The electrode 10c is the same as the electrode 10b shown and described with respect to FIGS. 3 and 3a of the drawings. However, the insulating layer 6b equivalent to the insulating layer 6 is extended so as to terminate along the same edge as that of the backing tape 8. Two parallel cuts 20, 21 are provided in the backing tape 8, the substrate 1 and the insulating layer 6b. The cuts 20, 21 extend substantially parallel with respect to the intermediate portion 13a and terminate along a notional line 22 perpendicular to the portion 13a and tangential to or in substantially parallel spaced apart relationship relative to, a notional line tangential to the sensor end 11a.

In use, therefore, that part of the electrode 10c bounded by the lines 20, 21 and 22 may be hingedly moved along the line 22 as shown in FIG. 4a of the drawings. That part 30 of the backing tape 8 indicated as 8a and 8b will remain in contact with the skin of the patient. Accordingly, the part 30 is free to move angularly, laterally or torsionally relative to the sensor end 11a without disturbing the sensor end 11a.

The electrodes 10b and 10c are suitable for applications which require long term, durable adhesion.

Figure 5:
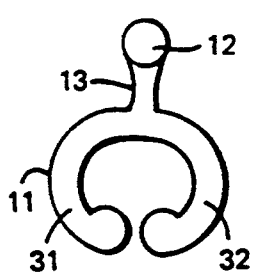
FIGS. 5, 5a and 5b are plan views of part of the electrodes according to the invention.
Figure 5A:
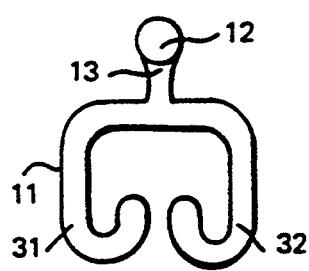
Figure 5B:
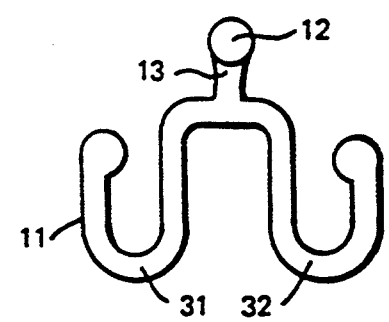

In FIGS. 5, 5a and 5b of the drawings there is shown examples of different shapes or patterns of conductive layer 2 which may be applied to the substrate 1 to form electrodes according to the invention. The sensor end 11 comprises two arms 31, 32 which provide a relatively large external surface area commensurate with a relatively small volume of conductive layer 2. In FIGS. 5a and 5b of the drawings, the arms 31, 32 may, for example, be extended with additional curves or arms either within the hollow or void or externally thereof as shown in FIG. 5b of the drawings. This can enhance the effectiveness of the electrode by providing a more even distribution of current throughout the gel layer (not shown). In addition, it is within the scope of the present invention to provide for an electrically conductive ink layer in which additional arms emanate from the interconnecting portion. Otherwise, the construction of said electrodes is similar to those previously described.

The electrodes according to the invention and particularly the electrode 10 are of particularly simple construction, relatively inexpensive to manufacture and of relatively low cost. The electrodes are designed for use in the monitoring or recording of biosignals such as ECG, EMG, EEG or in the application or transmission of relatively small amplitude electric currents or voltages to the body, as in electrical impedance tomography.

The invention is not limited by or to the specific embodiments described which can undergo considerable variation without departing from the scope of the invention.

We claim:

1. A biosignal electrode, comprising: a flexible substrate having an obverse side and a reverse side, an electrically conductive layer printed on the obverse side and comprising an ink having electrically conductive particles or a mixture of particles therein, the electrically conductive layer in plan view defining a first, sensor end, a second, connecting end, and an interconnecting portion, and means for encouraging a current to flow to peripheral edges of the sensor end, said encouraging means comprising the sensor end in plan view resembling a hollow figure, and the substrate at or near the sensor end being continuous and imperforate.

2. A biosignal electrode as claimed in claim 1 wherein the figure is a curved shaped figure.

3. A biosignal electrode as claimed in claim 1 or claim 2 wherein the figure is a closed figure.

4. A biosignal electrode as claimed in claim 3 wherein the figure is an annulus.

5. A biosignal electrode as claimed in any of claims 1 or 2 wherein the particles comprise silver or tin.

6. A biosignal electrode as claimed in any of claims 1 or 2 wherein the mixture of particles comprises silver/silver salt or tin/tin salt.

7. An electrode as claimed in any of claim 1 which further comprises an electrolytic gel layer, the conductive layer being interposed between the gel layer and the substrate.

8. An electrode as claimed in claim 7 wherein the electrolytic gel layer is located on the sensor end of the substrate.

9. An electrode as claimed in claim 7 or claim 8 wherein the gel layer is located on the sensor end.

10. An electrode as claimed in any of claim 7 wherein the gel layer comprises a conductive adhesive.

11. An electrode as claimed in claim 7 wherein an electrically insulating layer is located on the connecting end and on the interconnecting portion and is in substantially co-planar relationship relative to the gel layer.

12. An electrode as claimed in any of claim 1 wherein means is provided for enabling an electrical connection to be made between the connection end and monitoring equipment.

13. An electrode as claimed in claim 12 wherein the electrical connection means comprises an electrically conductive snap fastener riveted through the substrate and in electrical communication with the conductive layer.

14. An electrode as claimed in any of claim 1 wherein an adhesive layer is located on the substrate in substantially co-planar relationship relative to the conductive ink layer.

15. An electrode as claimed claim 14 wherein the adhesive layer is located on the obverse side of the sensor end of the substrate within the void of the hollow figure and in substantially co-planar relationship relative to the conductive layer.

16. An electrode as claimed in claim 14 wherein the reverse side has an adhesive element thereon which element extends outwardly relative to the substrate so as to provide an adhesive surface for enabling the electrode to be in dermal contact with a patient.

17. An electrode as claimed in any of claim 16 wherein the connecting end, the interconnecting portion and that part of the adhesive element in register with the connecting end and the intermediate portion are movable relative to the remainder of the adhesive element when in use.

18. An electrode as claimed in claim 1 wherein the substrate is electrically conductive.

19. An electrode as claimed in claim 1 wherein the mixture of particles comprises silver/silver chloride is a ratio of 9:1 by weight.

20. An electrode as claimed in claim 1 wherein the conductive layer has a thickness of between 5 and 15 microns.

21. An electrode as claimed in claim 1, wherein an outer edge of the sensor end is roughened to increase a perimeter-to-area ratio.

* * * * *